US00PP12432P2

(12) United States Plant Patent
Kent

(10) Patent No.: US PP12,432 P2
(45) Date of Patent: Mar. 5, 2002

(54) BROMELIAD PLANT NAMED 'GUZ 226'

(75) Inventor: Jeffrey C. Kent, Encinitas, CA (US)

(73) Assignee: Kent's Bromeliad Nursery, Inc., Vista, CA (US)

( * ) Notice: Subject to any disclaimer, the term of this patent is extended or adjusted under 35 U.S.C. 154(b) by 0 days.

(21) Appl. No.: 09/659,637

(22) Filed: Sep. 12, 2000

(51) Int. Cl.[7] ..... A01H 5/00
(52) U.S. Cl. ..... Plt./371
(58) Field of Search ..... Plt./371, 370

(56) References Cited

U.S. PATENT DOCUMENTS

PP11,682 P * 12/2000 Kent ..... Plt./371

* cited by examiner

*Primary Examiner*—Bruce R. Campell
*Assistant Examiner*—June Hwu
(74) *Attorney, Agent, or Firm*—James A. Lucas; Driggs, Lucas, Brubaker & Hogg Co., LPA

(57) ABSTRACT

A Bromelaid hybrid having intense red purple bracts and an appearance similar to that of of the European hybrid 'Amaranth' but lighter in color and smaller in size.

1 Drawing Sheet

BACKGROUND OF THE INVENTION

This application relates to a newly developed interspecific hybrid Guzmania plant resulting from a planned breeding program that I conduct on an ongoing basis. The objects of the breeding program include the crossing of selected parent plants from the numerous, compatible species within the genus, to obtain plants with novel and attractive phenotypes, coloration, and flowering forms. Other important selection factors may include ultimate plant size and shape, disease resistance, tolerance to different soil and growing conditions and vigor.

Among the objects of my program are to produce plants of the Bromelaiceae family which will be attractive to the consumer; which will develop reasonably rapidly under controlled conditions, and which retain for a long term, highly attractive and bright inflorescence; i.e., bract coloration, after being induced into the flowering stage. It is a specific object to provide a low maintenance plant which will be a long term decorative appointment offering an exotic color splash in the home of a buyer, or to serve as a substitute for flowering plants which have a shorter flowering duration in, for example, indoor plant and flower scapes. Finally, it is an object to develop plants which may be easily and efficiently multiplied by state-of-the-art tissue culture methods while continuing the distinctive characteristics of the plants through progressive clonal generations.

The plant of this disclosure was a selection from the progeny resulting from the cross of a seed parent Guzmania 'Dominica' (unpatented) with a pollen parent *Guzmania wittmackii* 'Pink' (unpatented). With the recognition that this seedling from the cross satisfied the objects of the breeding program, the individual was isolated and set aside for further observation and testing. The resulting selection has been assigned the designation 'GUZ 226' for purposes of identification. This plant has been reproduced by tissue culture at Evergem Belgium, and the clonal specimens resulting have been determined to be identical to the original selection in all distinguishing characteristics. The superior attributes of this plant will be revealed in the botanical descriptions to follow.

SUMMARY OF THE INVENTION

The attributes of the Guzmania hybrid designated as 'GUZ 226', which distinguish it from the other similar Guzmania hybrids are described as follows:

The pollen parent brings a tall columnar growth habit, large spaces between the scape bracts, and a bract that has a medium pink-red-purple coloration. The seed parent is smaller and more compact than the pollen parent. The spaces between the scape bracts of the seed parent are much smaller, and the bract color is a medium red-purple. The resultant seedling is between the two parents in size, more compact than either and with intense red-purple bracts. The seedling resembles the European hybrid 'Amaranth' (unpatented) but without the dark purple-violet color of 'Amaranth'. It is somewhat smaller and appears to be more disease resistant than Guzmania 'Amaranth'. 'GUZ 226' is relatively fast growing, reaching marketability in less than two years from a 1" plant. It remains in good color for 12 to 14 weeks under interior light conditions.

BRIEF DESCRIPTION OF THE DRAWING

The single color photograph of the drawing depicts a mature specimen of the plant in mid to late flowering stage. The age of the observed plant is 24 months. The plant was grown under greenhouse conditions in coastal southern California. Observations were made at mid afternoon in July. Illustrated are the mature leaves, scape bract and primary bract. The color definitions in the specification have been taken from The R.H.S. Colour Chart of The Royal Horticultural Society. The colors depicted are believed to be of a high level of color fidelity and are believed to be as close to the actual coloration of the plant as possible in a photographic illustration of this quality. However, due to factors such as light reflectance, cultural conditions and horticultural practices, the coloration of this plant should be understood to be approximate. For example, the bract color might slightly fade if the plant is subjected to bright light and the leaf color may vary depending on the composition and the concentration of fertilizer which may be applied to the plant.

BOTANICAL DESCRIPTION OF THE PLANT

Genus and species: Guzmania hybrid.
Parentage:
*Seed parent.*—Guzmania 'Dominica'.
*Pollen parent.*—*Guzmania wittmackii* 'Pink'.

Propagation: Method of Asexual Reproduction — Tissue Culture. Where reproduction took place: Reginald De Roose BVBA DROOGTE 139, B9940 Evergem, Belgium.

Plant:

*Type-monocot perennial.*—Diploid.

*General characteristics.*—Medium in size: Overall height from soil including inflorescence — 16" to 18". Overall width — 29" to 31".

*Habit.*—Spreading and open. Vase formed. Hardiness at temperatures below 32° F.: tender.

Leaves:

*Number.*—16–19.

*Medium in size.*—Length 18"–20"; Width: 1¼" to 1½" (mid length).

*Shape.*—Lanceolate; tip acuminate and narrowly pointed.

*Surface texture.*—Smooth.

*Thickness.*—Medium.

*Margin.*—Smooth. Apetiolate.

*Coloration.*—RHS 137-B in color obverse and reverse, some faint straining RHS 61-A in color obverse and reverse, particularly on upper leaves. Upper leaves also colored RHS 67-C at the base fading to RHS 67-D halfway to the apex. The remainder of the color is RHS 137-B to the apex. Some longitudinal plication occurs particularly on upper leaves of some plants at anthesis.

*Inflorescence a branched spike.*—Overall inflorescence is 8.5" to 9.5" and 14"–16" tall.

Scape bracts:

*Size.*— 5¾"×1¼" to 2"×¾"×1" at apex, (Width measured at midlength). Shape: Ovate, narrowly acuminate, clasping, margin is entire. Number: 10–12. Color: RHS 64-A obverse and reverse.

*Surface texture.*—Smooth.

Primary bracts:

*Size.*— 2½"×9/16" (measured at midlength). Lanceolate in shape broadly acute, margin is entire. Color: RHS 67-B obverse and reverse, somewhat translucent at tip.

*Surface texture.*—Smooth.

Floral buds: Tubular, gamosepalous.

*Size.*—2.5" long by 1" wide.

*Color.*—9D.

*Form.*—Tubular.

*Sepals.*—3 in number. Size — 0.75 long. Color — 61B.

*Petals.*—Size — 1.25" long by ⅛ wide.

Flowers: Morphology as for Guzmania. Clusters glomerule. Apetiolate, scarcely open at anthesis. Medium in size — 2.5" long by 1" wide. Sepals 1¼"×¼" translucent, 3 in number; acuminate. Petals 1½"×1¼" translucent; color paler than RHS 155-D; 3 in number; joined 1" from base; gamopetalous. Corolla — cylindrical.

Reproductive organs:

*Stamens.*—5 in number. Anthers: Color: 1C. Length: ⅛". Filaments: Color: 2D. Length: ¼".

*Pollen.*—Color: 1D.

*Pistil.*—Number: 1. Color: 2D.

*Style.*—Length: 11/16".

*Ovaries.*—Superior, enclosed in calyx, 3 locules.

Fruit: A three celled capsule splitting longitudinally when mature, Seeds with pappus-seeds not viable.

Resistance to disease and pests: None observed.

What is claimed is:

1. A new and distinct variety of Guzmania plant named 'GUZ 226' as illustrated and described herein.

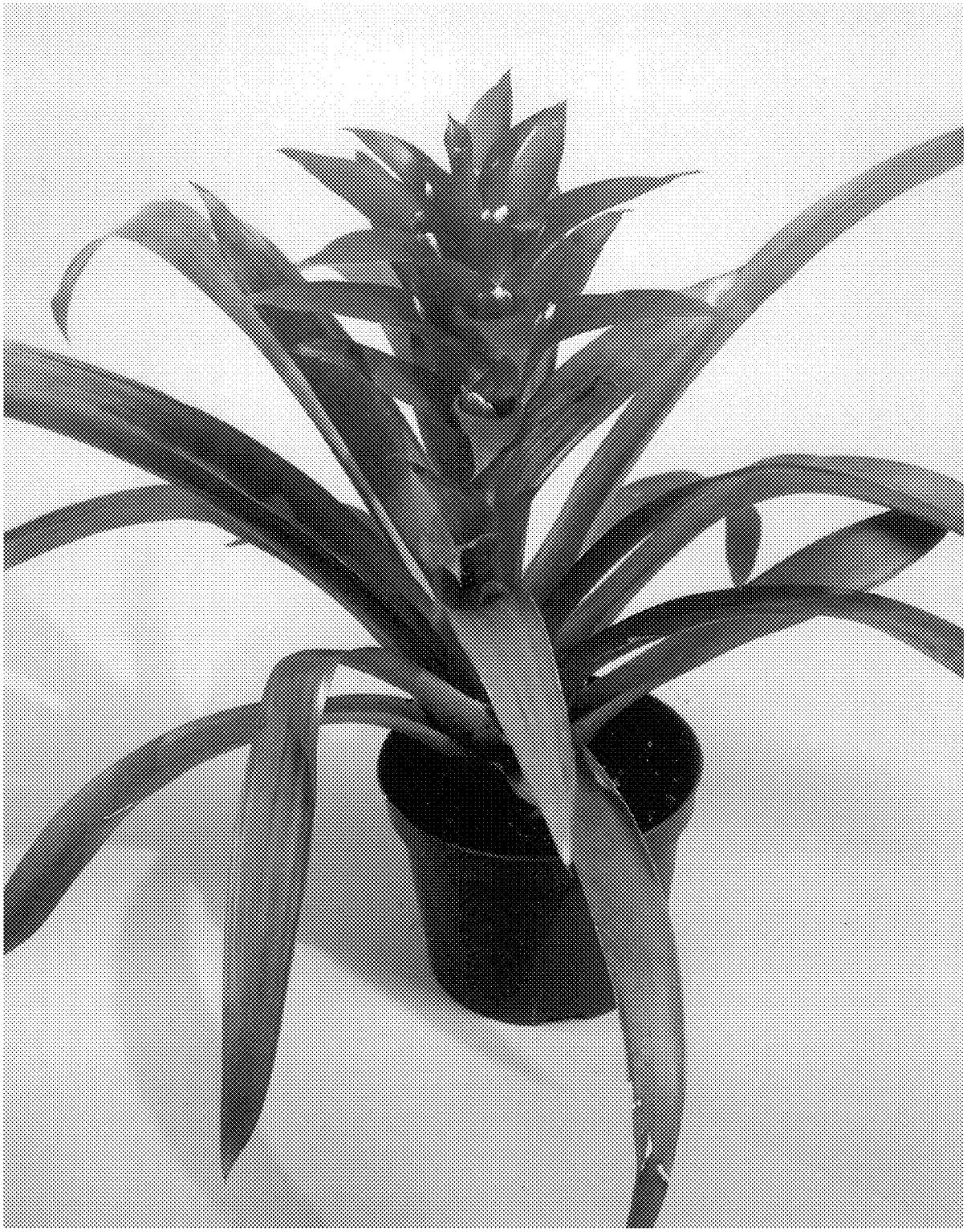

* * * * *